US00PP11027P

United States Patent [19]

Bergman

[11] Patent Number: Plant 11,027

[45] Date of Patent: Aug. 10, 1999

[54] HIBISCUS PLANT NAMED 'MANGO BREEZE'

[75] Inventor: Wendy R. Bergman, Lehigh Acres, Fla.

[73] Assignee: Yoder Brothers, Inc., Barberon, Ohio

[21] Appl. No.: 08/995,361

[22] Filed: Dec. 29, 1997

[51] Int. Cl.[6] ..... A01H 5/00

[52] U.S. Cl. ..... Plt./257

[58] Field of Search ..... Plt./67.8, 257

[56] References Cited

PUBLICATIONS

Usher. The Wordsworth Dictionary of Botany. p. 274, 1966.

*Primary Examiner*—Elizabeth Kemmerer
*Assistant Examiner*—Melissa L. Kimball
*Attorney, Agent, or Firm*—C. A. Whealy

[57] ABSTRACT

A new and distinct cultivar of Hibiscus plant named 'Mango Breeze', characterized by its dark green leaves; upright and outwardly spreading, uniform and symmetrical plant habit that is appropriate for container production; floriferousness with numerous salmon-colored flowers with dark red to purple throats; good resistance to flower bud abscission; and excellent postproduction longevity.

1 Drawing Sheet

The present invention relates to a new and distinct cultivar of Hibiscus, botanically, known as *Hibiscus rosa-sinensis*, and hereinafter referred to by the cultivar name Mango Breeze.

The new cultivar is a product of a planned breeding program conducted by the inventor in Alva, Fla. The objective of the breeding program is to create new Hisbiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of a proprietary *Hibiscus rosa-sinensis* selection, designated as code number 511, as the female, or seed, parent with the *Hibiscus rosa-sinensis* cultivar Vista (disclosed in U.S. Plant Pat. No. 6,608) as the male, or pollen, parent. The cultivar Mango Breeze was discovered and selected by the inventor as a flowering plant within the progeny of the stated cross in a controlled environment in Alva, Fla., on Jul. 12, 1994.

Compared to plants of the female parent, the proprietary Hibiscus selection code number 511, plants of the new Hibiscus flower about one week earlier, have larger flowers and differ in flower color. Plants of the new Hibiscus differ in flower color and have significantly more flowers than plants of the male parent, the cultivar Vista.

Asexual reproduction of the new cultivar by terminal cuttings taken in a controlled environment in Alva, Fla., has shown that the unique features of this new Hibiscus are stable and reproduced true to type in successive generations.

The cultivar Mango Breeze has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Mango Breeze'. These characteristics in combination distinguish 'Mango Breeze' as a new and distinct cultivar:

1. Dark green leaves.
2. Upright and outwardly spreading, uniform and symmetrical plant habit that is appropriate for container production.
3. Very freely flowering, numerous salmon-colored flowers with dark red to purple throats.

4. Good resistance to flower bud abscission.
5. Excellent postproduction longevity.

Plants of the new Hibiscus can be compared to plants of the nonpatented cultivar Euterpe. However, in side-by-side comparisons conducted in Alva, Fla., plants of the new cultivar differ from plants of the cultivar Euterpe in the following characteristics:

1. Plants of the new Hibiscus are more compact than plants of the cultivar Euterpe.
2. Plants of the new Hibiscus are more floriferous than plants of the cultivar Euterpe.
3. Flowers of plants of the new Hibiscus are darker in color than flowers of plants of the cultivar Euterpe.
4. Plants of the new Hibiscus flower about 14 days earlier than plants of the cultivar Euterpe.
5. Flowers of plants of the new Hibiscus have a ruffled petal margin and more substance than flowers of plants of the cultivar Euterpe.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of typical plant of 'Mango Breeze'.

The photograph at the bottom of the sheet comprises a close-up view of a typical flower of 'Mango Breeze'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The R.H.S. Colour Chart except where general terms of ordinary dictionary significance are used.

Botanical classification: *Hibiscus rosa-sinensis* cultivar Mango Breeze.

Parentage:

*Female or seed parent.*—*Hibiscus rosa-sinensis* proprietary selection designated as code number 511.

*Male or pollen parent.*—*Hibiscus rosa-sinensis* cultivar Vista, disclosed in U.S. Plant Pat. No. 6,608.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright to outwardly spreading, inverted triangle, uniform and symmetrical plant habit. Moderate vigor.

*Branching habit.*—Freely branching, usually five to six lateral branches develop after removal of terminal apex.

*Plant height, soil level to top of flowers.*—About 40 cm.

*Plant diameter, area of spread.*—About 50 cm.

*Lateral branch description.*—Length: About 30 cm. Diameter: About 7.5 mm. Texture: Immature, smooth; woody with age.

*Color.*—Immature: Close to 200B. Mature: Grayish green.

Foliage description:

*Arrangement.*—Alternate, single.

*Length.*—About 9.5 cm.

*Width.*—About 8 cm.

*Shape.*—Mostly cordate.

*Apex.*—Acute.

*Base.*—Cordate.

*Margin.*—Crenate.

*Texture.*—Glabrous and glossy/shiny on both surfaces.

*Color.*—Young foliage, upper surface: Brighter and greener than 146A. Young foliage, lower surface: 146A. Mature foliage, upper surface: Dark green, darker than 147A. Mature foliage, lower surface: Darker than 147B.

*Petiole.*—Length: About 3.5 cm. Diameter: about 2.75 mm. Texture: Smooth or with very fine pubescence on upper surface. Color: Close to 200B.

Flower description:

*Natural flowering season.*—Usually spring and summer or during periods of warm weather.

*Flower arrangement.*—Flowers arranged singly at terminal leaf axils. Very freely flowering with usually about five flower buds and/or open flowers per terminal apex. Flowers flat and face upright.

*Flower appearance.*—Star-shaped single. Salmon-colored petals with dark red to purple throat. Flowers are open for about one day before closing. Flowers self-cleaning.

*Flower diameter.*—About 12.5 cm.

*Flower bud* (*just before showing color*).—Rate of opening: About one day depending on temperatures. Length: About 2.5 cm. Diameter: About 9 mm. Shape: Columnar, oblong.

*Petals.*—Texture: Crepe, ruffled. Arrangement: Corolla consists of five petals that overlap. Shape: Spatulate with rounded apex. Margin: Entire, but ruffled. Length: About 7.5 cm. Width: About 5.25 cm. Color: Opening: Close to 41A/41B. Upper surface: 48A; veins, 51B, 51A at base. Lower surface: Shiny, mostly 51A and 50A; veins, 53A. Yellowish at right edges of petals with dark pink speckles. Throat: Dark red to purple, 53A to 59A.

Sepals: Appearance: Six sepals fused into a star-shaped calyx. Shape: Linear. Texture: Smooth. Color, outer surface: Brighter and greener than 146A.

*Peduncles.*—Length: About 4 cm. Diameter: About 3 mm at apex. Angle: Upright. Strength: Strong, rigid. Color: 144A.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 8 cm. Style color: Apex: 51B. Base: 46A to 47A. Stigma number: Five. Stigma shape: Round. Stigma diameter: About 1.5 mm. Stigma color: 46A. Ovary color: Light green, 154A/154B.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Mango Breeze', as illustrated and described.

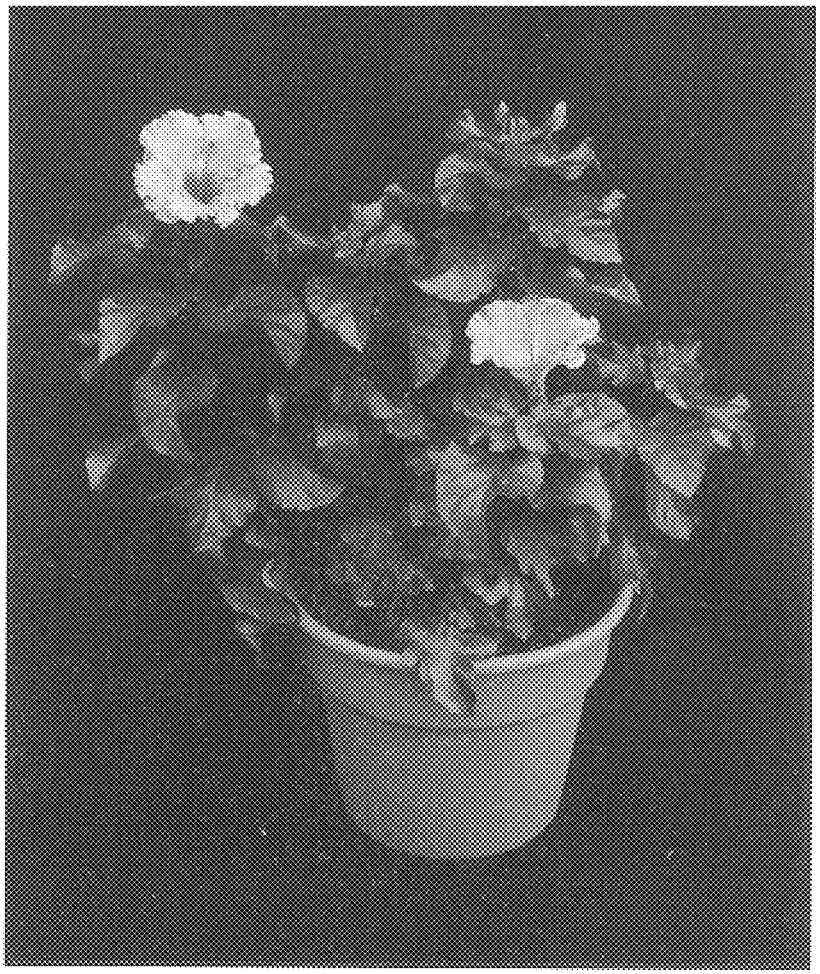
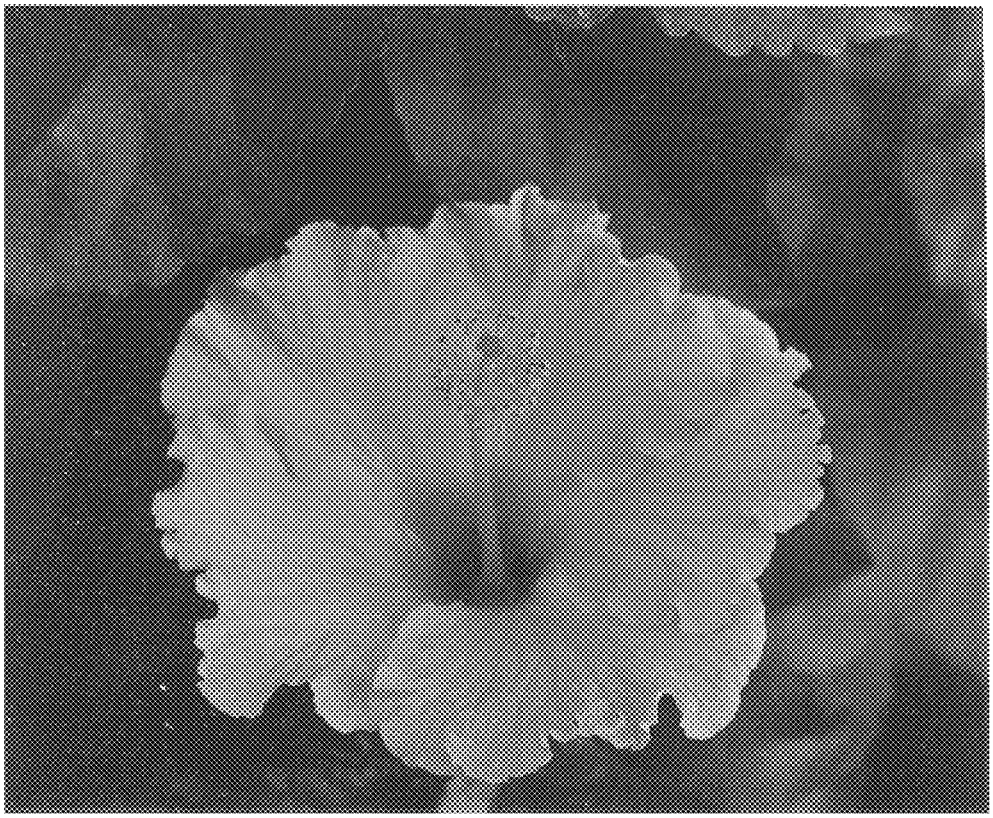

* * * * *